(12) United States Patent
Littmann et al.

(10) Patent No.: US 6,550,481 B1
(45) Date of Patent: Apr. 22, 2003

(54) METHOD FOR PRODUCING AN ORTHOPEDIC CUSHION HAVING A SOFT ELASTIC REGION

(75) Inventors: Alexander Littmann, Isernhagen (DE); Reinhold Schneider-Nieskens, Adendorf (DE); Hans Georg Blau, Burgwedel (DE)

(73) Assignee: Thämert Orthopädische Hilfsmittel GmbH & Co. KG, Burgwedel (DE)

( * ) Notice: Subject to any disclaimer, the term of this patent is extended or adjusted under 35 U.S.C. 154(b) by 148 days.

(21) Appl. No.: 09/667,308

(22) Filed: Sep. 22, 2000

(51) Int. Cl.7 .............................. A61G 15/00
(52) U.S. Cl. ......................... 128/845; 602/1
(58) Field of Search .................. 128/845, 846, 128/869, 878, 879, 888; 602/1, 41, 8, 20–23

(56) References Cited

U.S. PATENT DOCUMENTS

RE28,688 E * 1/1976 Cook .................... 260/4
4,700,698 A    10/1987  Kleylein
5,027,801 A    7/1991   Grim
5,306,229 A    4/1994   Brandt et al.

FOREIGN PATENT DOCUMENTS

DE  87 00 681       3/1987
FR  2 712 487       5/1995
WO  WO 97/24085     7/1997
WO  WO 99/09917     3/1999

* cited by examiner

Primary Examiner—Michael A. Brown
(74) Attorney, Agent, or Firm—Collard & Roe, P.C.

(57) ABSTRACT

A method of producing cushions having soft elastic inserts for use with orthopedic devices, comprising placing a cushion on a supporting surface and pouring a free-flowing material into the cushion to form the insert. The free-flowing material is then solidified, producing a soft elastic insert and is simultaneously secured to the cushion.

20 Claims, 2 Drawing Sheets

METHOD FOR PRODUCING AN ORTHOPEDIC CUSHION HAVING A SOFT ELASTIC REGION

BACKGROUND OF THE INVENTION

1. Field of the Invention

The invention relates to a method for producing a cushion with at least one soft elastic region. In particular, the invention comprises a felt cushion with a silicone pad for use with orthopedic devices.

2. The Prior Art

It is known that such cushions are used in orthopedic devices such as epicondylitis braces. This is accomplished by using a felt cushion, which is adapted to the shape of the epicondylitis brace, and has silicone points in its end areas which come into contact with the skin of the user in a special manner, thereby preventing the cushion from slipping.

These felt cushions are produced by introducing a recess into the felt cushion and gluing a prefabricated silicone spot of the same size in this recess. Such orthopedic devices are known from WO 97/24085 and WO 99/09917.

SUMMARY OF THE INVENTION

An object of the present invention is to provide a method for producing a cushion for use with orthopedic devices which can be easily manufactured and is inexpensive.

The method according to the invention comprises injecting a free-flowing material into a cushion to form a soft elastic region, and solidifying the free-flowing material in the region. This makes it possible to produce a cushion with a soft elastic area rapidly, inexpensively and extremely easily.

A cushion having a recess is preferably placed on a supporting surface, and then the free-flowing material is introduced into the recess to form the soft elastic insert. The free-flowing material flows into the recess of the cushion and is then solidified. In this case, a cushion with a soft elastic insert is created in an especially simple and rapid manner, whereby the cushion and the soft elastic insert are bonded together. This takes place through the injection of the free-flowing material within the recess, whereby the free-flowing material flows to the cushion, adheres to the cushion and then is solidified. In this case, an insert with an exact fit is produced, in one operation, while at the same time being bonded to the cushion. As an alternative, a cushion without a recess can also be used.

In a preferred embodiment, the soft elastic insert is made of silicone, which is introduced into the recess in the form of a liquid and then vulcanized. In addition, it is advantageous if the free-flowing material poured into the recess is actively distributed. Essentially, it is also possible to have only the free-flowing material flowing in the recess. After a short period of time, a uniform layer develops. It is advantageous if the supporting surface is aligned to be absolutely horizontal. In another embodiment of the invention, the supporting surface is heated to approximately 70–120° Celsius, so that the solidification of the material and the vulcanization of the silicone can be adjusted by the temperature setting. The vulcanization time of silicone amounts to between one minute and several hours, depending on the temperature and the catalyst content. It is preferred that the temperature be adjusted so that the vulcanization time is approximately two to three minutes, because otherwise the silicone will soak too deep into the cushion. At a vulcanization time of two to three minutes, the silicone runs to the edge of the recess and to the edge of the cushion and fuses with the cushion at the edges and vulcanizes fully. After the desired vulcanization time, the cushion is removed from the heated supporting surface to cool.

In an alternative embodiment, the cushion does not have a recess, rather it is designed as a continuous piece. This cushion is stretched on a cushion mount, which has a recess in the position where the region for forming the silicone pad is provided. The free-flowing material is poured into the recess of the cushion mount, and is vulcanized forming a cushion on which is arranged a pad extending above the cushion and fused with the cushion.

In another preferred embodiment, the cushion is stretched on a cushion mount having a recess aligned with the recess in the cushion. The cushion and cushion mount are placed together on a supporting surface. This is accomplished by arranging the cushion between the supporting surface and the cushion mount, i.e., the cushion rests directly on the supporting surface and the cushion mount is arranged above it. The cushion mount is mechanically secured so that it exerts a force on the cushion and the cushion rests on the supporting surface to seal it. The femur fracture material poured into the recess in the cushion and remains inside the recess and cannot escape through gaps. It is advantageous to use a cushion mount which is adapted in shape to that of the cushion. Therefore, not only is the recess exposed, but also the cushion can be pressed onto the supporting surface in the common area.

In another preferred embodiment, a soft coating is applied to one side of the cushion. This soft coating is designed with a hook strip, i.e. a VELCRO®-type closure. In this case, the cushion with the soft coating can be attached to the cushion mount with corresponding hook strips arranged on the cushion mount. The cushion is then placed on the supporting surface on the side opposite the side having the soft coating. Flush sealing silicone pads or silicone spots are produced on the side of the cushion on the bottom facing the supporting surface. The pads are in contact with the patient's body, thereby preventing the cushion from slipping. The recess of the cushion mount is preferably filled with the free-flowing material to form the insert. Therefore, an insert can be designed thicker than the cushion itself, or with any desired height. The insert or the silicone pad preferably has a height of one to two millimeters.

This method can be performed such that several cushion mounts are operated simultaneously. Therefore, several cushions can be placed on the supporting surface at the same time and the free-flowing material is poured into the recesses in these cushions and solidified at the same time. In this way, it is economically feasible to produce large lot sizes.

In another preferred embodiment, the supporting surface is profiled so that the silicone regions produced can have a desired shape. Concave or convex designs of the heated contact surface are possible. A concave design of the supporting surface, i.e., a hollow or inward curving shape, is especially preferred, so that the silicone region is shaped with a convex curvature on the outside. Thus, on the whole this yields a felt cushion with a silicone region curving outward, projecting slightly and therefore it can contact the user's skin especially well and thus prevent slipping.

A cushion having a soft elastic region, in particular a silicone pad, can be produced by the method described here, where the cushion is fused to the soft elastic region in a bordering area. This bordering area is preferably about 1 mm thick. The soft elastic region can be fused to the cushion on its lower side. As an alternative, the soft elastic region is fused to the cushion on its outer edge. Such a cushion is especially simple to produce, and it prevents separate gluing of the soft elastic region to the rest of the cushion.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF A PREFERRED EMBODIMENT

Figure 1:
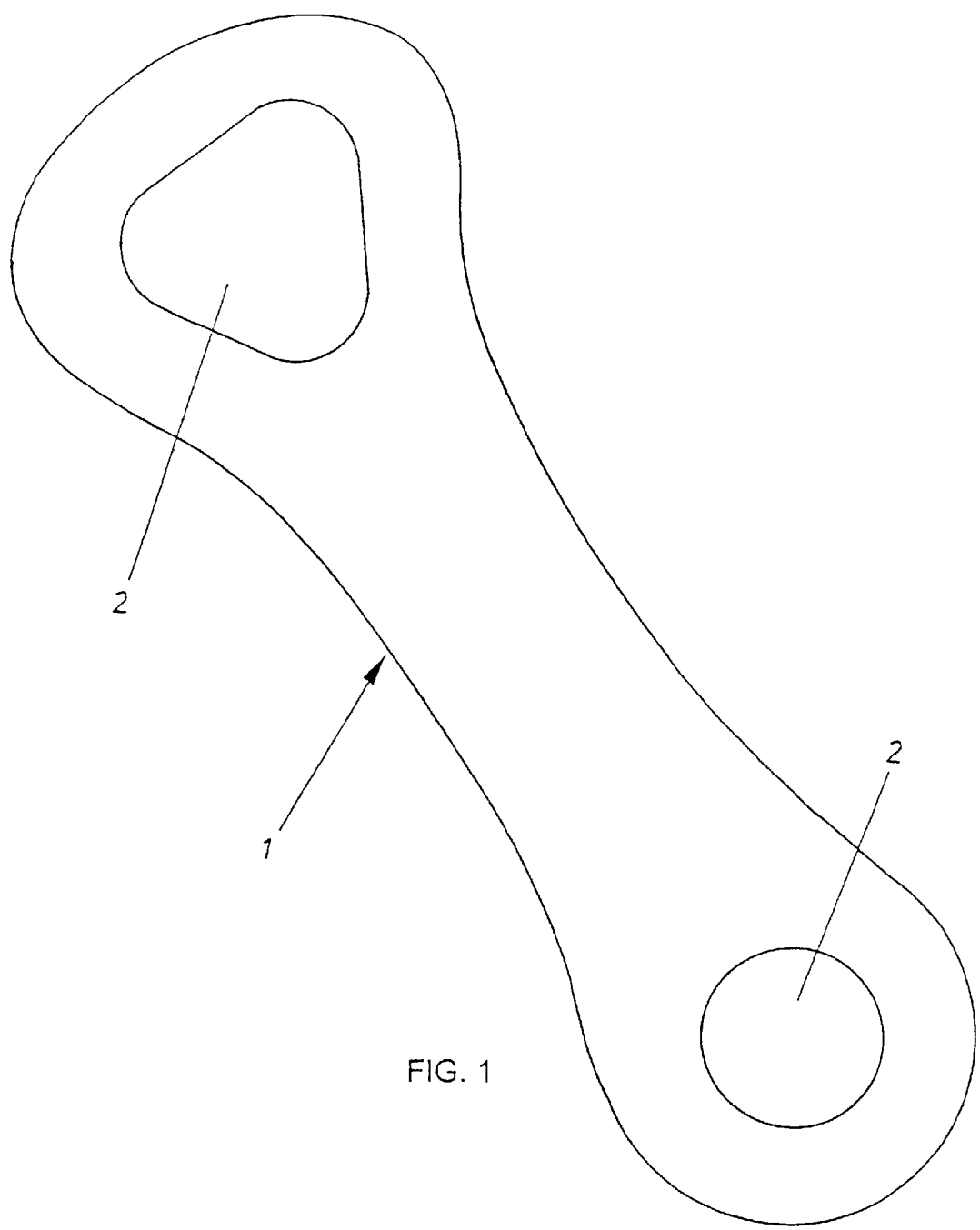
FIG. 1 shows a top view of a cushion produced according to the invention.
Figure 2:
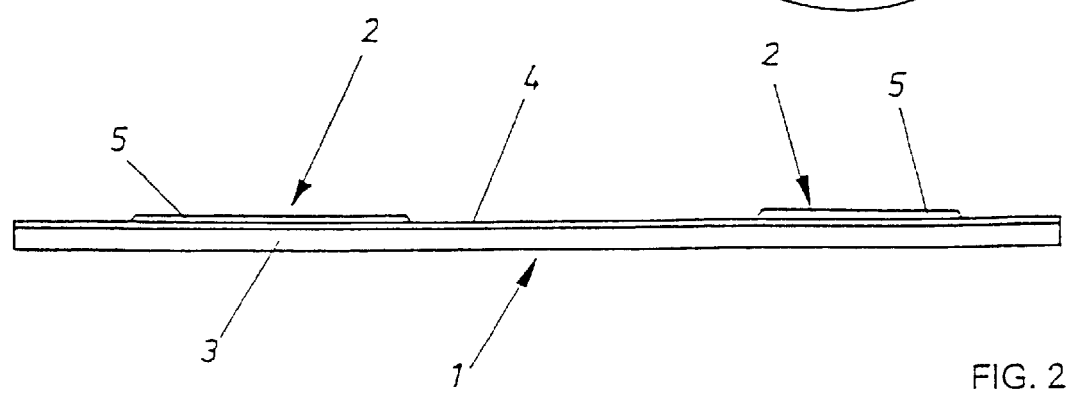
FIG. 2 shows a side view of the cushion.

FIG. 1 shows a cushion 1 which is intended for use in an epicondylitis brace. The shape of the cushion is adapted to an epicondylitis brace, and soft elastic inserts 2 are arranged in the enlarged end areas, so that they rest on the skin and prevent cushion 1 from slipping. FIG. 2 shows a side view of cushion 1. In its lower area, cushion 1 is made of a felt layer 3 with a soft coating 4 arranged thereon, designed so that it can be joined via a VELCRO®-type fastener. Inserts 2 may be designed such that they project a distance 5 above insert 1. This projecting distance is usually arranged on the side on which soft coating 4 is provided, since cushion 1 is placed on the supporting surface with the side on which felt 3 is arranged during production.

Figure 3:
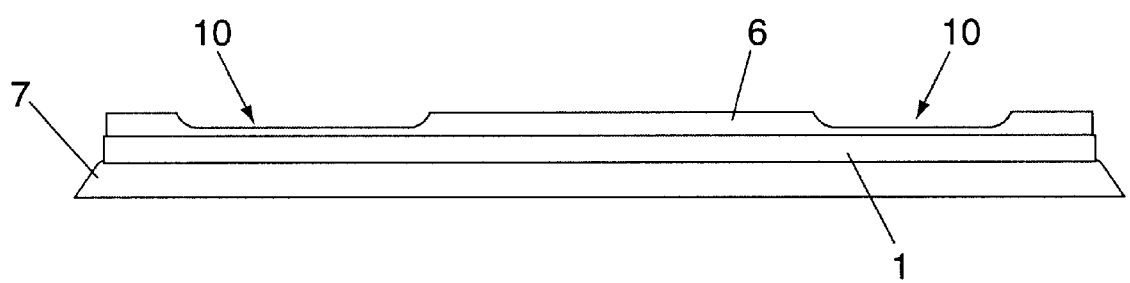
FIG. 3 shows the cushion on the cushion mount and support surface.

With the production process according to the invention, cushions of the desired shape and size are punched out of a padding material, i.e., preferably a felt cushion with a soft coating arranged on it. Recesses are also punched out for the subsequent inserts or pads. Felt cushion 1 punched out in this way is attached by its soft coating layer 4 to a cushion mount 6, as shown in FIG. 3, with the VELCRO®-type fastener. A plurality of cushion mounts arranged side by side are usually used, with one cushion attached to each by the VELCRO®-type fastener. Cushion mounts 6 have approximately the same contour as cushion 1. Cushion mounts 6 are then folded down together with a holding strip and strapped to a heatable supporting surface 7. Supporting surface 7 is preferably formed by an aluminum sheet which is heated to a temperature of 70° to 120° Celsius. In addition, crosslinking silicone with a suitable hardness is poured into recess 10 in cushion 1 and cushion mount 6 above it. The silicone flows to the border of the felt and cushion mount, fuses to the edges with the felt and is vulcanized. The vulcanization time is between one minute and up to several hours, depending on the temperature and the catalyst content. A vulcanization time of approximately two to three minutes has proven especially advantageous, because then the silicone has soaked so far into the felt such that it fuses thereto. If the vulcanization time is longer, there is the risk that the silicone will soak too far into the material of the cushion. The arrangement of cushion 1 with its felt side 3 on the supporting surface ensures that cushion 1 with its soft elastic inserts or its silicone pads is designed to be flat and flush. On the opposite side, silicone or some other soft elastic material can be poured through the cushion mount resting on the cushion up to a height which projects beyond the height of cushion 1. It is also possible to vary the height of the silicone pad on the rear side. A height of 1 to 2 mm is preferred. In an alternative process, cushion 1 which does not have any recesses is attached to a cushion mount by a VELCRO®-type fastener. Cushion mount 6 has recesses 10 which are provided in the areas where the soft elastic regions are to be produced. The soft elastic material, preferably silicone, is introduced through recesses 10 in cushion mount 6, so that a layer approximately 1 to 2 mm thick is produced. The temperature, vulcanization time and viscosity of the material are selected so that it soaks in approximately 1 mm and is fused thereto. After the end of the vulcanization time, which amounts to about 8 to 10 minutes, the cushions can be removed from the cushion mount. In this manner, a cushion is produced with a soft elastic region arranged on the cushion.

Accordingly, while only a few embodiments of the present invention have been shown and described, it is to be understood that many changes and modifications may be made thereunto without departing from the spirit and scope of the invention.

What is claimed is:

1. A method for producing a cushion with at least one soft elastic region, comprising the steps of: filling the cushion with a free-flowing material forming a soft elastic region; and solidifying said free-flowing material.

2. The method according to claim 1, wherein said cushion comprises a recess for forming said soft elastic region.

3. The method according to claim 2, wherein the method further comprises the step of placing said cushion on a supporting surface; pouring said free-flowing material into said recess to form a soft elastic region designed as an insert; and solidifying said free-flowing material in the recess.

4. The method according to claim 3, wherein said soft elastic insert comprises liquid silicone poured into said recess and then vulcanized.

5. The method according to claim 2, further comprising the step of distributing said free-flowing material poured into said recess.

6. The method according to claim 3, further comprising the step of heating said supporting surface.

7. The method according to claim 4, wherein said vulcanization step takes two to three minutes.

8. The method according to claim 3, wherein said cushions are attached to cushion mounts having a recess aligned with said soft elastic region.

9. The method according to claim 8, wherein said cushion is arranged between said supporting surface and said cushion mount.

10. The method according to claim 8, wherein said cushion mount is mechanically secured, wherein said cushion mount comprises a shape adapted to the cushion.

11. The method according to claim 8, further comprising the step of applying a soft coating to one side of said cushion.

12. The method according to claim 11, wherein said cushion having said soft coating is attached to the cushion mount.

13. The method according to claim 11, further comprising placing said cushion on said supporting surface, wherein the cushion side opposite the side having said soft coating rests on said supporting surface.

14. The method according to claim 8, wherein said recess in said cushion mount is filled with silicone.

15. The method according to claim 8, further comprising pouring said free-flowing material into recesses of several cushion mounts, and solidifying said free-flowing material in recesses of the different cushion mount at the same time.

16. The method according to claim 3, wherein said supporting surface comprises a concave shape to form the soft elastic insert.

17. A cushion with a soft elastic region, in particular a felt cushion having a silicon pad, wherein the cushion is fused to the soft elastic region in a bordering area.

18. The cushion according to claim 17, wherein said bordering area is approximately 1 mm thick.

19. The cushion according to claim 17, wherein the soft elastic region is fused to the felt cushion on its lower side.

20. The cushion according to claim 17, wherein the soft elastic region is fused to the felt cushion on its outer edges.

* * * * *

UNITED STATES PATENT AND TRADEMARK OFFICE
CERTIFICATE OF CORRECTION

PATENT NO.     : 6,550,481 B1
DATED          : April 22, 2003
INVENTOR(S)    : Littmann et al.

It is certified that error appears in the above-identified patent and that said Letters Patent is hereby corrected as shown below:

<u>Title page,</u>
Item [30], following Item [22], insert:

-- [30] Foreign Application Priority Data
September 25, 1999  (DE) ............ 199 46 058.2 --

Signed and Sealed this

Sixteenth Day of September, 2003

JAMES E. ROGAN
*Director of the United States Patent and Trademark Office*